United States Patent [19]

Disteldorf et al.

[11] Patent Number: 4,483,798

[45] Date of Patent: Nov. 20, 1984

[54] POLYADDITION PRODUCTS CONTAINING URETIDIONE GROUPS AND PROCESS FOR THEIR PREPARATION

[75] Inventors: Josef Disteldorf; Rainer Gras; Werner Hübel, all of Herne; Elmar Wolf, Recklinghausen; Horst Schnurbusch, Herne, all of Fed. Rep. of Germany

[73] Assignee: Chemische Werke Huls Aktiengesellschaft, Herne, Fed. Rep. of Germany

[21] Appl. No.: 292,500

[22] Filed: Aug. 13, 1981

[30] Foreign Application Priority Data

Aug. 13, 1980 [DE] Fed. Rep. of Germany ....... 3030572

[51] Int. Cl.$^3$ ............................................. C07D 229/00
[52] U.S. Cl. ................................... 260/239 A; 528/59
[58] Field of Search .................................... 260/239 A

[56] References Cited

FOREIGN PATENT DOCUMENTS 1934763 1/1971 Fed. Rep. of Germany .
2420475 11/1975 Fed. Rep. of Germany .
1153815 5/1969 United Kingdom .

*Primary Examiner*—Dolph H. Torrence
*Attorney, Agent, or Firm*—Oblon, Fisher, Spivak, McClelland & Maier

[57] ABSTRACT

A method for producing a polyaddition product of isophorone diisocyanate and diols which comprises, reacting a uretidione group-containing dimer of isophoronediisocyanate, which is decomposable by heat into 98% isophorone diisocyanate, with a diol, wherein the ratio of NCO to OH groups is such that the final polyaddition product has free terminal NCO groups, or free terminal OH groups.

13 Claims, No Drawings

POLYADDITION PRODUCTS CONTAINING URETIDIONE GROUPS AND PROCESS FOR THEIR PREPARATION

BACKGROUND OF THE INVENTION

1. Field of the Invention

The present invention relates to uretidione group-containing polyaddition products.

2. Description of the Prior Art

Polyaddition products containing uretidione groups are known and have been described, for example, in German OS No. 2,420,475. Such compounds are produced by reaction of the uretidione derived from toluene diisocyanate or hexamethylene diisocyanate with diols or diamines. The uretidione derived from isophorone diisocyanate also should be suitable for preparing the polyaddition compounds containing uretidione groups claimed in German OS No. 2,420,474; however, there are therein no examples or detailed disclosures.

The lack of examples and the like is not surprising, because the prerequisite for preparing a polyaddition compound containing uretidione groups is that the uretidione-containing diisocyanate, used for chain-extension with diols, have an NCO functionality of 2. When the NCO functionality of the uretidione-containing isocyanate is greater than 2, at least partial gelling has to be expected when it is reacted, for example, with diols.

With the dimerization catalysts of the prior art (tert. phosphines), it has not been possible until now to produce an isocyanurate-free uretidione dimer of isophorone diisocyanate (IPDI). A uretidione dimer of isophorone diisocyanate produced according to German OS No. 1,670,720 or OS No. 1,934,739 contains ca. 20–40% b.w. of the trimer of IPDI (isocyanurate of isophorone diisocyanate) in the mixture, depending on the reaction conditions. Such an uretidione dimer of isophorone diisocyanate containing isocyanurate cannot be considered for use in preparing valuable starting materials for polyurethane chemistry by further reaction, for example, with diols.

This further reaction could only be possible if pure, isocyanurate-free uretidione dimer of isophorone diisocyanate is used. The preparation of this material in pure form, free from admixed uretidione derivatives containing isocyanurate, and capable of being more than 98% decomposed back into isophorone diisocyanate by heating, is not the object of this patent application. The material is prepared by dimerizing isophorone diisocyanate, optionally in an inert organic solvent, with the help of a catalyst of the general formula:

$$X_mP(NR_2)_{3-m}$$

wherein m=0, 1, 2

X: Cl, OR, R

R: identical, different alkyl, aralkyl or (optionally substituted) cycloalkyl radicals, or 2R groups together form a ring with the N atom, at temperatures of 0°–80° C., preferably 10°–30° C., and the resulting 1,3-diazacyclobutane-2,4-dione is isolated from the reaction mixture after 5–70% has reacted, preferably 20–50%, without previously deactivating the catalyst, as the residue of a thin film distillation and the catalyst and monomer are isolated as the distillate.

The uretidione dimer of IPDI produced in this manner is highly viscous at room temperature (>10⁶ mPa·s; at 60° C. 13×10³ mPa·s; at 80° C. 1.4×10³ mPa·s). Its NCO content lies in the range of 16.8–18% NCO; i.e. greater or lesser proportions of polymeric uretidiones derived from IPDI must be present in the reaction product. The monomer content is <1%. The NCO content of the reaction product after heating to 180°–200° C. is 37.1–37.7% NCO.

In the reaction of the uretidine dimers of IPDI with diols, the NCO/OH ratio should be 1:0.5–1:0.9 or 0.5:1–0.9:1. Depending on this ratio the uretidione-containing polyaddition products may contain free terminal NCO groups or, in special cases, terminal OH groups.

For certain applications it has proved convenient to react the free terminal NCO groups of the polyaddition product, the uretidione dimer of isophorone diisocyanate, with diols completely or at least partially with monoalcohols or primary or secondary monoamines.

SUMMARY OF THE INVENTION

Accordingly, an object of the invention is a method of preparing polyaddition products containing uretidione groups from an isophorone diisocyanate derivative containing uretidione groups characterized in that a uretidione group-containing derivative of isophorone diisocyanate, which is 98% decomposable by heat back into isophorone diisocyanate, is reacted with diols, wherein the NCO/OH ratio is 1:0.5–1:0.9, or 0.5:1–0.9:1, and optionally reacting the addition product so obtained partially or completely with monoalcohols or monoamines.

Further objects of the invention are polyaddition products containing uretidione groups, prepared as claimed, from uretidione-group containing derivatives of isophorone diisocyanate, which are up to 98% decomposable by heat back into IPDI, and diols, and, optionally, monoalcohols or monoamines.

DETAILED DESCRIPTION OF THE PREFERRED EMBODIMENTS

In reacting the uretidione dimer of isophorone diisocyanate with the diol, the process can be carried out by adding the diol all at once or gradually to the uretidione dimer of isophorone diisocyanate.

Examples of such dihydric alcohols are: ethylene glycol, 1,2- and 1,3-propylene glycol, 2-ethyl-1,3-hexanediol, 1,6-hexanediol, 1,8-octanediol, neopentyl glycol, 1,4-bis(hydroxymethyl)cyclohexane, 3(4),8(9)-bis(-hydroxymethyl)tricyclodecane, 2-methyl-1,3-propanediol, 3-methyl-1,5-pentanediol, diethylene glycol, triethylene glycol, tetraethylene glycol, dipropylene glycol and dibutylene glycol. It is preferable to use 1,4-butylene glycol as a linking diol to form the polyuretidione-polyurethane according to the invention.

In carrying out the reaction, the reagents are mixed in the given ratios. In general, as already described, one begins with the isocyanate component and adds the diol. The reaction can take place neat or in suitable solvents. Suitable solvents are, for example, benzene, toluene, methyl- or ethylglycol acetate, dimethylformamide, xylene and other aromatic or aliphatic hydrocarbons; also ketones such as acetone, methyl butyl ketone, methyl isobutyl ketone, cyclohexanone and chlorinated aromatic hydrocarbons, as well as any mixture of these with other inert solvents.

The reaction generally takes place at temperatures between 50°–120° C., preferably 60°–90° C. The reaction components are held at the given temperatures until all OH groups have reacted to form urethane groups. This takes 0.5–5 hrs., depending on the reaction temperature. Catalysts which accelerate the isocyanate polyaddition reaction can also be used; preferred catalysts are organic tin compounds, such as tin(II) acetate, tin(II) octoate, tin(II) laurate, dibutyltin diacetate, dibutyltin dilaurate, dibutyltin maleate or dioctyltin acetate. The catalysts are generally added in amounts between 0.01 and 0.5% b.w. based on the total amount of the reactants used.

The reaction mixture is generally worked up by separating the polyuretidione-polyurethane from any solvent used. This can be done by simply removing the solvent in a vacuum. Particularly suited for removing the solvent is melt extrusion in an evacuated screw.

In addition, reaction products which are particularly advantageous are those which are obtained by reaction of the described addition compounds of the uretidione dimer of isophorone diisocyanate and diols with monoalcohols. The reaction of the addition compounds with the monoalcohols is carried out so that all, or at least a portion, of the terminal NCO groups are reacted with monoalcohols. The procedure is such that the uretidione dimer of isophorone diisocyanate is reacted with the diol under the conditions described above and, following completion of the reaction, the mixture is not cooled, but rather the temperature is maintained and the monoalcohol is added to the reaction mixture. Heating of the reaction mixture is then continued until an equivalent amount of NCO is reacted for each OH that is added. The reaction products are isolated in the manner described above.

Suitable monohydric alcohols are: methanol, ethanol, n-butanol, 2-ethylhexanol, n-decanol, cyclohexanol. The uretidione-containing polyaddition products with monoalcohols are particularly suitable for use as binders for PUR powder enamels, which do not split off blocking agent when they are cured.

Primary or secondary monoamines can be used in place of monoalcohols. Suitable monoamines are, e.g., n-propylamine, n-butylamine, n-hexylamine, dibutylamine, dicyclohexylamine.

In the reaction of uretidione-containing polyaddition products with primary or secondary monoamines, it is recommended that the amine be added in portions, because the $NH_2$/NCO reaction proceeds very quickly, with the release of large amounts of heat. Isolation of the reaction products is carried out as described above.

Further advantageous polyaddition compounds of the uretidione dimer of isophorone diisocyanate and diols are those having terminal OH groups, i.e. the uretidione is reacted with the diol in an NCO/OH ratio of 0.5:1–0.9:1.

The polyaddition products of the invention, namely:
1. adducts having free terminal NCO groups
2. those whose NCO groups are completely or partially reacted with monoalcohols or monoamines; and
3. those with terminal OH groups, are generally compounds whose molecular weight range is 900–5,000, preferably 1,000–3,000. The polyaddition products have a melting point of 80°–140° C., preferably 100°–130° C. They are particularly suited as curing agents for polyfunctional (thermoplastic) compounds containing Zerewitinoff-active hydrogen atoms. In combination with such compounds containing Zerewitinoff-active hydrogen atoms, the polyaddition products form valuable synthetic resin systems curable at temperatures above 140° C., preferably 160°–180° C. The most important area of application for such systems is their use as binding agent components for PUR powder enamels and single-component stoving enamels. The compounds according to the invention may be used as intermediates for the production of plastics, enamels, and foam products. Accordingly, they are particularly valuable, because, due to their low vapor pressure they are physiologically harmless. They are especially well suited for the production of solvent-containing and low-solvent single- and dual component PUR enamels, such as coil coating or high solids enamels, and PUR powder enamels, as well as solvent-free single- and dual component coatings.

EXAMPLE A:

Preparation of Uretidione-containing Derivatives of Isophorone Diisocyanate 100 p.b.w. of isophorone diisocyanate were mixed with 1 p.b.w. of tris(dimethylamino)phosphine and allowed to stand for 20 h at room temperature. The NCO content of this mixture after this time amounted to 31% b.w., i.e., ca. 40% of the isophorone diisocyanate had reacted. Then this mixture was subjected to thin film distillation at 130° C. and 0.1 torr. The residue was free of catalyst and had an NCO content of 17.6%. When the residue was heated 30–60 min. at 180° C., the NCO content increased to 37.1–37.7%. This so-called "hot value" was a direct measure of the content of uretidione groups in the reaction product.

EXAMPLE B:

Preparation of Adducts of the Uretidione Dimer of Isophorone Diisocyanate General Preparation Guidelines The uretidione dimer of isophorone diisocyanate produced according to A is prepared, optionally in a solvent such as acetone, methylene chloride, toluene or xylene, and heated to 50°–100° C. It is briskly stirred in an inert gas atmosphere, and the diol is added to the uretidione dimer of isophorone diisocyanate so that the reaction temperature does not exceed 110° C. The reaction is monitored by titrimetric NCO determination, and is terminated after 2–5 hrs. at ca. 100° C. When the free NCO groups are to be partially or completely blocked, the necessary amount of alcohol is added and the reaction is allowed to proceed to completion at 110° C. The progress of the reaction is also monitored by titrimetric NCO determination. After cooling and possibly evacuating and drying, and optionally crushing the reaction product, a light yellow, free flowing powder is obtained. The IR-spectrum of the cross-linking product exhibits the characteristic intense bands of the uretidione groups at 1,760–1,780 $cm^{-1}$; depending on the degree of blocking, no, or only weak, NCO bands are detectible by IR-spectroscopy.

| | Uretidione-Containing Adducts | | | | | | | |
|---|---|---|---|---|---|---|---|---|
| | Starting Materials | | | | Reaction Products | | | |
| Example | IPDI-uretidione mole | Diol Mole | | monoalcohol | | Total NCO-% | Free NCO-% | Melting Pt °C. | DTA °C. |
| 1 | 2 | 1 | B | | | 25.11 | 7.6 | 81–86 | 41–55 |
| 2 | 3 | 2 | B | | | 22.14 | 4.6 | 93–96 | 45–57 |
| 3 | 4 | 3 | B | | | 20.5 | 3.3 | 98–102 | 49–60 |
| 4 | 5 | 4 | B | | | 19.4 | 2.5 | 100–106 | 47–61 |
| 5 | 4 | 5 | B | | | 11.8 | <0.1 | 97–105 | 50–60 |
| 6 | 3 | 2 | HD | | | 21.1 | 4.4 | 76–81 | 45–55 |
| 7 | 4.5 | 3.5 | HD | | | 19.1 | 2.8 | 77–82 | 44–53 |
| 8 | 5 | 4 | HD | | | 18.9 | 2.4 | 80–85 | 47–58 |
| 9 | 3 | 2 | MP | | | 20.9 | 4.6 | 75–78 | 44–55 |
| 10 | 5 | 4 | MP | | | 18.6 | 2.7 | 80–84 | 47–57 |
| 11 | 4.5 | 3.5 | NPG | | | 19.3 | 2.7 | 81–86 | 48–57 |
| 12 | 4.5 | 3.5 | DEG | | | 19.2 | 2.8 | 78–80 | 42–51 |
| 13 | 4.5 | 3.5 | EG | | | 20.5 | 2.9 | 81–85 | 43–52 |
| 14 | 4 | 3 | DMC | | | 18.8 | 3.0 | 86–91 | 49–59 |
| 15 | 4.5 | 3.5 | TMH | | | 18.0 | 2.5 | 75–81 | 42–51 |
| 16 | 3 | 2 | B | 1 | EH | 16.68 | 1.05 | 104–108 | 55–65 |
| 17 | 3 | 2 | B | 2 | EH | 15.21 | 0.48 | 95–100 | 53–58 |
| 18 | 4 | 3 | B | 1 | EH | 17.81 | 1.62 | 110–115 | 56–61 |
| 19 | 4.5 | 3.5 | B | 1 | EH | 17.88 | 1.2 | 107–118 | 62–69 |
| 20 | 4.5 | 3.5 | B | 2 | EH | 16.2 | 0.2 | 104–110 | 60–70 |
| 21 | 4.5 | 3.5 | B | 2 | M | 16.8 | 0.4 | 108–117 | 58–67 |
| 22 | 4.5 | 3.5 | B | 2 | E | 16.7 | 0.3 | 106–111 | 59–68 |
| 23 | 4.5 | 3.5 | EG | 2 | EH | 16.4 | 0.35 | 108–119 | 61–71 |
| 24 | 4.5 | 3.5 | HD | 2 | EH | 15.8 | 0.51 | 102–107 | 58–63 |
| 25 | 4.5 | 3.5 | MP | 2 | EH | 15.7 | 0.41 | 101–109 | 57–66 |
| 26 | 4.5 | 3.5 | B | 1 | M | 18.1 | 1.3 | 110–115 | 62–78 |
| 27 | 4.5 | 3.5 | B | 2 | DBA | 15.3 | 0 | 117–123 | 65–77 |

B 1,4-butanediol
DBA dibutylamine
DEG diethylene glycol
DMC 1,4-bis(hydroxymethyl)cyclohexane
E ethanol
EG ethylene glycol
EH 2-ethylhexanol
HD 1,6-hexanediol
M methanol
MP 3-methyl-1,5-pentanediol
NPG neopentyl glycol
TMH 2,2,4 (2,4,4)-trimethyl-1,6-hexane diol

We claim:

1. A method for producing a polyaddition product of isophoronediisocyanate and diols which comprises:
reacting a uretidione dimer of isophorone diisocyanate, which is 98% decomposable by heat into isophoronediisocyanate, with a diol, wherein the ratio of NCO to OH groups is such that said polyaddition product has free terminal NCO groups, or free terminal OH groups.

2. The method of claim 1 wherein the ratio of NCO to OH groups is 1:0.5–1:0.9 or 0.5:1–0.9:1.

3. The method of claim 1 wherein said polyaddition product has excess free terminal NCO groups.

4. The method of claim 1 wherein said polyaddition product has excess free terminal OH groups.

5. The method of claim 3 wherein said polyaddition product is further reacted with a monoalcohol, a primary monoamine or a secondary monoamine to totally or partially block said terminal NCO groups.

6. The method of claim 1 wherein said diols are selected from the group consisting of ethylene glycol, propylene-1,2-glycol, propylene-1,3-glycol, 2-ethylhexanediol-1,3, 1,6-hexanediol, 1,8-octanediol, neopentylglycol, 1,4-bis (hydroxymethyl) cyclohexane, 3(4), 8(9)-bis (hydroxymethyl) tricyclodecane, 2-methylpropane-1,3-diol, 3-methylpentane-1,5-diol, diethylene glycol, triethylene glycol, tetraethylene glycol, dipropylene glycol, dibutylene glycol, and 1,4-butyleneglycol.

7. The method of claim 5 wherein said polyaddition product is reacted with a monoalcohol selected from the group consisting of methanol, ethanol, n-butanol, 2-ethylhexanol, n-decanol and cyclohexanol.

8. The method of claim 5 wherein said polyaddition product is reacted with a primary or secondary monoamine selected from the group consisting of n-propylamine, n-butylamine, n-hexylamine, dibutylamine and dicyclohexyl amine.

9. The method of claim 1 wherein said reaction is carried out in a solution of a solvent and, which further comprises:
removing the solvent after the reaction is substantially complete.

10. A polyaddition product of the uretidinedione dimer of isophoronediisocyanate (IPDI) with diols, wherein said product is derived from a uretidinedione group-containing dimer of IPDI which is 98% decomposable by heat into IPDI; and
wherein said product has free terminal NCO groups or free end OH groups.

11. The product of claim 10 which has terminal NCO groups.

12. The product of claim 10 which has free terminal OH groups.

13. The product of claim 10 wherein said terminal NCO groups have been further reacted totally or partially with a monoalcohol, a primary monamine or a secondary monoamine.

* * * * *